(12) United States Patent
Chen et al.

(10) Patent No.: US 11,267,712 B2
(45) Date of Patent: Mar. 8, 2022

(54) TUNING PRODUCTS SELECTIVITY OF $CO_2$ REDUCTION REACTION WITH SURFACE LIGANDS

(71) Applicant: HONDA MOTOR CO., LTD., Tokyo (JP)

(72) Inventors: Shutang Chen, Powell, OH (US); Gugang Chen, Powell, OH (US)

(73) Assignee: HONDA MOTOR CO., LTD., Tokyo (JP)

( * ) Notice: Subject to any disclaimer, the term of this patent is extended or adjusted under 35 U.S.C. 154(b) by 442 days.

(21) Appl. No.: 16/156,604

(22) Filed: Oct. 10, 2018

(65) Prior Publication Data

US 2020/0115234 A1 Apr. 16, 2020

(51) Int. Cl.
*C01B 32/40* (2017.01)
*C07C 1/04* (2006.01)

(52) U.S. Cl.
CPC .............. *C01B 32/40* (2017.08); *C07C 1/043* (2013.01); *C07C 2531/24* (2013.01)

(58) Field of Classification Search
CPC ..... C01B 32/40; C07C 1/043; C07C 2531/24; C02B 32/40
USPC ........................................................ 502/165
See application file for complete search history.

(56) References Cited

U.S. PATENT DOCUMENTS

| 9,957,168 B2 * | 5/2018 | Harutyunyan | C01G 55/00 |
| 2019/0030523 A1 * | 1/2019 | Chen | B01J 23/94 |
| 2019/0316264 A1 * | 10/2019 | Chen | C25B 9/23 |

FOREIGN PATENT DOCUMENTS

| JP | 2005-536634 A | 12/2005 |
| JP | 2018-034136 A | 3/2018 |
| WO | WO 2012/124625 A1 | 9/2012 |

OTHER PUBLICATIONS

Communication dated Oct. 20, 2020, from the Japanese Patent Office in counterpart application No. 2019-183799.
Dongguo Li, et al, "Surfactant Removal for Colloidal Nanoparticles from Solution Synthesis: The Effect on Catalytic Performance", ACS Catalysis, 2012, 2, pp. 1358-1362.
Francisco Zaera, "The Surface Chemistry of Catalytic Reactions: Progress and Challenges", The Journal of Physical Chemistry Letters, 2015, 6, pp. 4115-4116.
Jens K. Norskov, et al., "Density functional theory in surface chemistry and catalysis", PNAS, Jan. 18, 2011, vol. 108, No. 3, pp. 937-943.
Manoj B. Gawande et al., "Cu and Cu-Based Nanoparticles: Synthesis and Applications in Catalysis", Chemical Reviews, 2016, 116, pp. 3722-3811.
Samir V. Jenkins et al, "Gold-copper alloyed nanorods for metal-catalyzed organic reactions: implication of surface ligands on nanoparticle-based heterogeneous catalysis", Tetrahedron Letters, 56, 2015, pp. 3368-3372.

(Continued)

*Primary Examiner* — Melissa S Swain
(74) *Attorney, Agent, or Firm* — Arent Fox LLP (57) ABSTRACT

Methods for preparing selective catalytic metal microstructures and nanostructures having at least one surface ligand. The methods include providing a preliminary metal microstructure or nanostructure having at least one preliminary surface ligand, and replacing the preliminary surface ligand with at least one surface ligand to provide the catalytic metal microstructure or nanostructure.

22 Claims, 6 Drawing Sheets

(56) References Cited

OTHER PUBLICATIONS

Shan Zhou et al., "Enabling Complete Ligand Exchange on the Surface of Gold Nanocrystals through the Deposition and Then Etching of Silver", Journal of The American Chemical Society.

Younan Xia, et al., "Shape-Controlled Synthesis of Colloidal Metal Nanocrystals: Thermodynamic versus Kinetic Products", Journal of the American Chemical Society, 2015, 137, pp. 7947-7966.

Zhili Wang, et al, "Engineering the internal surfaces of three-dimensional nanoporous catalysts by surfactant-modified dealloying," Nature Communications, 8, 1066.

Zhiqiang Niu et al., "Removal and Utilization of Capping Agents in Nanocatalysis", Chemistry of Materials, 2014, 26, 72-83.

* cited by examiner

TUNING PRODUCTS SELECTIVITY OF $CO_2$ REDUCTION REACTION WITH SURFACE LIGANDS

TECHNICAL FIELD

The present disclosure is directed generally to a method for preparing selective catalytic metal microstructures and nanostructures comprising at least one surface ligand.

BACKGROUND OF THE DISCLOSURE

Metal microstructures and nanostructures are often employed in various catalytic fields. For example, metal nanoparticles are frequently studied for use as catalysts in carbon dioxide ($CO_2$) reduction reactions. The surface chemistry of such structures is a critical aspect of these studies, as surface chemistry may affect the structures' synthesis and their potential application in catalytic fields. For example, the morphology and size of metal nanoparticles may be controlled by choosing proper organic ligands to cap specific facets of the nanoparticles, as these ligands will alert the nanoparticle's nucleation and growth rate during solution synthesis.

However, while ligands are often critical for tuning the shape and size of metal microstructures and nanostructures during synthesis, many known ligands are detrimental to the resulting structures' use in catalytic fields, as the ligands often block access to catalytic sites on the structures' surface. Moreover, longer ligands often affect the conductivity of the metal comprised by the structures.

To alleviate these problems, UV-Ozone irradiation, thermal annealing, and acid washing have recently been used for catalyst surface cleaning and surfactant removal. However, these methods often cause catalyst aggregation and induce size and morphology changes. There is thus a need in the art for a method for preparing catalytic metal microstructures and nanostructures having acceptable catalyst activity and product selectivity without inducing structure changes and aggregation.

BRIEF DESCRIPTION OF THE DISCLOSURE

The present disclosure is directed generally to a method for preparing selective catalytic metal microstructures and nanostructures comprising at least one surface ligand. According to some aspects, the method may comprise providing a preliminary metal microstructure or nanostructure comprising at least one preliminary surface ligand, and replacing the preliminary surface ligand with at least one surface ligand to provide the catalytic metal microstructure or nanostructure. The present disclosure is also directed to catalytic metal microstructures or nanostructures prepared by the methods described herein.

DETAILED DESCRIPTION OF THE DISCLOSURE

The present disclosure is directed generally to a method for preparing selective catalytic metal microstructures and nanostructures comprising at least one surface ligand. According to some aspects, the method may comprise providing a preliminary metal microstructure or nanostructure comprising at least one preliminary surface ligand, and replacing the preliminary surface ligand with at least one surface ligand to provide the catalytic metal microstructure or nanostructure. The present disclosure is also directed to catalytic metal microstructures or nanostructures prepared by the methods described herein.

As used herein, the term "microstructure" refers to an acceptable catalytic structure having dimensions on the microscale, for example, a structure having dimensions from 0.1 to 100 microns. Examples of microstructures include, but are not limited to, microparticles, microsheets, microwares, microcubes, and micropolyhedrons. As used herein, the term "nanostructure" refers to any acceptable catalytic structure having dimensions on the nanoscale, for example, a structure having dimensions from 0.1 to 100 nanometers. Examples of nanostructures include, but are not limited to, nanoparticles, nanosheets, nanowires, nanocubes, and nanopolyhedrons. It should be understood that when aspects of the present disclosure are discussed herein in regard to a structure, the discussion relates to any acceptable microstructure or nanostructure according to the present disclosure.

According to some aspects, the microstructure or nanostructure may comprise a metal acceptable for use as a catalyst, particularly metals suitable for, at least in part, catalyzing $CO_2$ reduction reactions. Examples of such metals include, but are not limited to, copper, iron, cobalt, nickel, silver, palladium, alloys thereof, and combinations thereof.

According to some aspects, the method may comprise preparing a preliminary metal structure comprising at least one preliminary surface ligand. As used herein, the term "surface ligand" refers to an ion or molecule attached to a surface of a structure by coordinate bonding. It should be understood that a "preliminary surface ligand" refers to a surface ligand wherein at least a portion thereof is replaced by a different surface ligand to provide the metal structure according to the present disclosure.

According to some aspects, the preliminary surface ligand may have a first coordination strength with respect to one or more metals comprised by the metal structure. As used herein, the term "coordination strength" refers to the strength of the coordination interaction between a metal atom and one or more atoms of a ligand. It should be understood that the coordination strength may correspond to the relative ability of a ligand to donate or share their available pair(s) of electrons.

According to some aspects, the preliminary surface ligand may comprise a ligand that is useful for preparing a metal structure having an acceptable shape and/or size. The preliminary surface ligand may be selected such that it, at least in part, controls structure (e.g., particle) aggregation. For example, the preliminary surface ligand may be selected to reduce and/or eliminate particle aggregation due to steric effect. According to some aspects, the preliminary surface ligand may be selected such that it coordinates with surface atoms of a selected metal structure in order to tailor the structure's surface energy, which may affect potential applications of the metal structure. Examples of ligands useful as preliminary surface ligands according to the present disclosure include, but are not limited to, oleylamine, trioctylphosphine (TOP), tetradecylamine, dodecylamine, octadecylamine, hexadecylamine, trioctylphosphine oxide, oleic acid, and combinations thereof.

According to some aspects, the preliminary surface ligand may have a length that is greater than about the length of a $C_5$ alkane molecule, optionally greater than about the length of a $C_6$ alkane molecule, optionally greater than about the length of a $C_7$ alkane molecule, optionally greater than about the length of a $C_8$ alkane molecule, optionally greater than about the length of a $C_9$ alkane molecule, and optionally greater than about the length of a $C_{10}$ alkane molecule.

According to some aspects, preparing a preliminary metal structure may comprise any known method in the art for preparing a metal structure comprising one or more preliminary surface ligands as described herein. For example, preparing the preliminary metal structure may comprise preparing a metal complex and reacting the metal complex with a preliminary surface ligand to provide the preliminary metal structure.

According to some aspects, the metal complex may comprise complexes of one or more metals as disclosed herein with one or more complexing agents. Complexing agents useful according to the present disclosure include, but are not limited to, tetradecylamine (TDA), dodecylamine (DDA), hexadecylamine (HAD), octadecylamine (ODA), and oleylamine (OLA). According to some aspects, the metal complex may be provided by combining one or more metals and/or salts thereof with one or more complexing agents in a solution under an inert atmosphere and stirring for an acceptable length of time at an acceptable temperature. For example, the metal complex may be provided by combining a metal salt and one or more complexing agents in a solution under an inert gas flow from about one minute to about one hour. Examples of inert gases include, but are not limited to, nitrogen gas, argon gas, and combinations thereof. The combined solution may then be heated to a temperature of between about 100 and 300° C. from about one minute to about one hour to provide a metal complex solution comprising the metal complex.

According to some aspects, the preliminary metal structure may be prepared by combining a metal complex as described herein with one or more preliminary surface ligands. For example, if the preliminary surface ligand comprises TOP, the preliminary metal structure may be prepared by combining the metal complex solution as described herein with TOP under an inert atmosphere and stirring for an acceptable length of time at an acceptable temperature, for example, at a temperature of between about 200 and 400° C. from about one minute to about one hour. After the acceptable length of time, the combined solution may be cooled, washed, and/or separated (e.g., centrifuged) to provide the preliminary metal structure.

According to some aspects, the method may comprise replacing the preliminary surface ligand of the preliminary metal structure with at least one surface ligand to provide the catalytic metal structure according to the present disclosure.

According to some aspects, the at least one surface ligand may comprise a ligand that provides acceptable catalytic activity when provided as part of a catalytic metal structure. Providing acceptable catalytic activity may comprise, for example, providing acceptable access to catalytic sites on the metal structure surface. Providing acceptable catalytic activity may comprise providing a metal structure having an acceptable current density. According to some aspects, the at least one surface ligand may provide acceptable catalytic activity without substantially changing the shape and/or size of the metal structure. Furthermore, the method of the present disclosure may limit and/or reduce oxidation of the catalytic metal structure.

According to some aspects, the at least one surface ligand may have a length that is shorter than the length of the preliminary surface ligand. According to some aspects, the at least one surface ligand may have a length that is less than about the length of a $C_{12}$ alkane molecule, optionally less than about the length of a $C_{11}$ alkane molecule, optionally less than about the length of a $C_{10}$ alkane molecule, optionally less than about the length of a $C_9$ alkane molecule, optionally less than about the length of a $C_8$ alkane molecule, optionally less than about the length of a $C_7$ alkane molecule, and optionally less than about the length of a $C_6$ alkane molecule.

The at least one surface ligand may be selected such that it, at least in part, controls structure (e.g., particle) aggregation. For example, the at least one surface ligand may be selected to reduce and/or eliminate particle aggregation due to steric effect. According to some aspects, the at least one surface ligand may be selected such that it coordinates with surface atoms of a selected metal structure in order to tailor the structure's surface energy, which may affect potential applications of the metal structure.

According to some aspects, the at least one surface ligand may be selected in order to provide a catalytic metal structure having an acceptable product selectivity. As used herein, the term "acceptable product selectivity" may refer to the characteristic of a catalytic metal structure that is capable of, at least in part, catalyzing a reaction such that the faradaic efficiency of at least one specific reaction product at a specific potential vs. RHE is at least about 20%, optionally at least about 30%, optionally at least about 40%, optionally at least about 50%, optionally at least about 60%, optionally at least about 70%, optionally at least about 80%, optionally at least about 90%, and optionally about 100%. For example, in the case of a $CO_2$ reduction reaction, the specific reaction product may consist of $H_2$, CO, $CH_4$, $C2H_4$, or a combination thereof.

According to some aspects, the one or more surface ligands may have a second coordination strength with respect to one or more metals comprised by the metal structure, wherein the second coordination strength is greater than the first coordination strength, that is, the coordination strength of the preliminary surface ligand with respect to the one or more metals comprised by the metal structure. Without wishing to be bound to a particular theory, by having a coordination strength that is greater than the coordination strength of the preliminary surface ligand, the one or more surface ligands may be capable of replacing the preliminary surface ligand on the metal structure's surface.

Ligands useful according to the present disclosure include, but are not limited to, hydrazine, ethylene diamine, propylene diamine, butane diamine, trimethylamine, acetic acid, propionic acid, butyric acid, valeric acid, octanethiol, ethanethiol, propanethiol, butanethiol, pentanethiol, hexanethiol, and combinations thereof.

According to some aspects, replacing the preliminary surface ligand of the preliminary metal structure with the one or more surface ligands may comprise combining the preliminary metal structure with the one or more surface ligands for an acceptable length of time. According to some aspects, from about 10 mg to 100 mg of the preliminary metal structure may be used to provide the catalytic metal structure. According to some aspects, the molar ratio of the preliminary metal structure to the one or more surface ligands used to prepare the catalytic metal structure may be between about 1:25 and 1:1000, optionally between about 1:25 and 1:750, and optionally between about 1:50 and 1:500. According to some aspects, the acceptable length of time may be between about one minute and four hours, optionally between about one hour and three hours, and optionally about two hours. According to some aspects, the preliminary metal structure and the one or more surface ligands may be combined under an inert atmosphere. According to some aspects, the preliminary metal structure and the one or more surface ligands may be combined at room temperature. As used herein, the term "room temperature" refers to a temperature between about 15 and 25° C. After the acceptable length of time, the combined solution may be washed and/or separated (e.g., centrifuged) to provide the catalytic metal structure according to the present disclosure.

Figure 1:
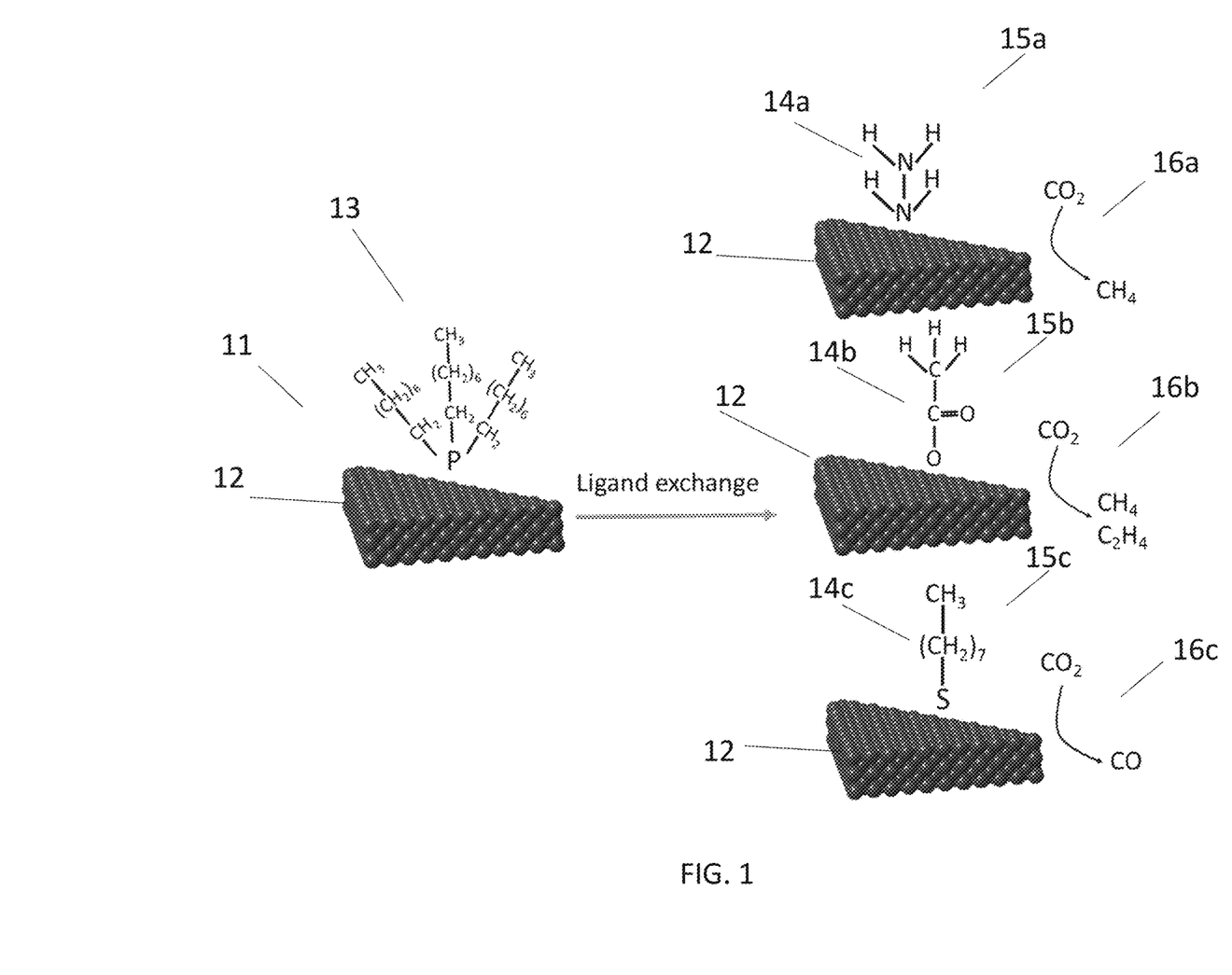
FIG. 1 shows a schematic of an example method according to aspects of the present disclosure.

FIG. 1 shows a schematic of an example method according to the present disclosure. In particular, FIG. 1 shows a preliminary metal structure 11 comprising a metal microsheet 12 and at least one preliminary surface ligand 13, in this example, TOP. As shown in FIG. 1, the catalytic metal structure may be prepared by replacing the preliminary surface ligand 13 with one or more surface ligands 14a, 14b, and/or 14c, in this example, hydrazine, acetic acid, and octanethiol, respectively. As shown in FIG. 1, the one or more surface ligands 14a, 14b, and/or 14c may be attached to a surface of the metal microsheet 12 by coordinate bonding. As shown in FIG. 1, the example method does not substantially affect the shape and/or size of the metal microsheet 12.

FIG. 1 also shows that the one or more surface ligands 14a, 14b, and/or 14c may be selected in order to provide a catalyst showing acceptable product specificity as described herein. In particular, FIG. 1 shows that catalytic metal structure 15a having surface ligand 14a, i.e., hydrazine, may show specificity toward $CO_2$ reduction reaction 16a, i.e., wherein $CO_2$ is reduced to $CH_4$. Similarly, FIG. 1 shows that catalytic metal structure 15b having surface ligand 14b, i.e., acetic acid, may show specificity toward $CO_2$ reduction reaction 16b, i.e., wherein $CO_2$ is reduced to $CH_4$ and $C_2H_4$. FIG. 1 also shows that catalytic metal structure 15c having surface ligand 14c, i.e., octanethiol, may show specificity toward $CO_2$ reduction reaction 16c, i.e., wherein $CO_2$ is reduced to CO. It should be understood that by selecting a specific surface ligand, a catalytic metal structure having an acceptable product selectivity may be obtained.

According to some aspects, the method as described herein may be applied to structures other than metal structures. For example, according to some aspects, the method as described herein may be applied to an inorganic microstructure or nanostructure and/or any microstructure or nanostructure wherein a specific surface ligand selection may be desired.

The present disclosure is also directed to catalytic metal structures as described herein. For example, the present disclosure is directed to a catalytic metal structure, such as a metal nanoparticle, comprising one or more of the metals as described herein and having one or more of the surface ligands as described herein attached to a surface thereof via coordinate bonding. The present disclosure is also directed to methods of using the catalytic metal structures as described herein, for example, by contacting $CO_2$ with the catalytic metal structure as part of a $CO_2$ reduction reaction.

The present disclosure is also directed to a device comprising the catalytic metal structures as described herein. According to some aspects, the device may be or may comprise an electrochemical cell, such as an electrochemical cell configured to perform $CO_2$ reduction reactions. According to some aspects, the electrochemical cell may comprise an anode, a cathode, an electrolyte, and/or a porous membrane. According to some aspects, the cathode and/or anode of the electrochemical cell may comprise the catalytic metal structures as described herein.

The present disclosure is also directed to a method of performing $CO_2$ reduction reactions using the catalytic metal structures as described herein. The method may comprise subjecting $CO_2$ to a device comprising the catalytic metal structures, such as the electrochemical cell as described herein, to reduce a portion or all of the $CO_2$ to a specific reaction product. According to some aspects, the specific reaction product may be selected from the group consisting of $H_2$, CO, $CH_4$, $C2H_4$, and combinations thereof.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

As used herein, the term "about" and "approximately" and "substantially" are defined to being close to as understood by one of ordinary skill in the art. In one non-limiting embodiment, the term "about" and "approximately" and "substantially" are defined to be within 10%, preferably within 5%, more preferably within 1%, and most preferably within 0.5%.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example I: Preparation of Metal Complex Solution 100 mg of copper (I) chloride (99.99%), 220 mg of tetradecylamine (TDA, >96%), and 2 mL of 1-octadecene (ODE 98%) were added into a flask where oxygen was removed under Ar or $N_2$ flow. After Ar or $N_2$ blowing for 20 minutes, the mixed solution was heated to 190° C. on a hot plate and kept at this temperature for 30 minutes. During the heating process, TDA was melted at 38~40° C. and coordinated with copper (Cu) atoms to form a Cu-TDA blue complex solution.

Example II: Preparation of Preliminary Metal Structure 6.0 mL of oleylamine (OLA 70%) was loaded in a 25 mL three-neck flask where oxygen was removed through Ar blowing for 20 minutes. 1.0 mL of TOP (97%) was injected into the flask under Ar flow. After 20 minutes of Ar flowing, the flask was rapidly heated to 300° C. Next, 2 mL of the Cu-TDA solution prepared according to EXAMPLE I was quickly injected into a hot flask. The reaction solution turned to red immediately. The reaction was held at 300° C. for 20 minutes. The reaction mixture was naturally cooled to 100° C., and 5 mL of hexane (or another hydrophobic solvent such as toluene or chloroform) was injected. The products were separated by centrifuging at 2000 rpm for 2 min. The supernatant was discarded. A total of 10 mL of hexane (or another hydrophobic solvent such as toluene or chloroform) was then added to the sediment, and the mixture was centrifuged at 2000 rpm for 3 min. The washing procedure was repeated twice to remove unreacted precursors and surfactant. The Cu nanosheets were stored in hydrophobic solvents (e.g., hexane, toluene, or chloroform) before characterization.

Example III(a): Preparation of Catalytic Metal Structure with Hydrazine 20 mg of Cu-TOP microsheets prepared according to EXAMPLE II and 4 mL of hydrazine hydrate (HZ, 50-60%) were loaded into a 25 mL flask. The reaction solution was stirred at room temperature under Ar flow for 2 hours. The products were separated by centrifuging at 2000 rpm for 2 minutes. The supernatant was discarded. A total of 5 mL of ethanol (or another hydrophilic solvent such as acetone or methanol) was then added to the sediment, and the mixture was centrifuged at 2000 rpm for 3 minutes. The washing procedure was repeated twice to remove unreacted precursors and surfactant. The resulting Cu-HZ microsheets were stored in hydrophilic solvents (for example, acetone, ethanol, or methanol) before characterization.

It was found that the amounts of Cu-TOP microsheets used may vary from 20 mg to 100 mg, and the volume of hydrazine used corresponds to the required reaction time.

Example III(b): Preparation of Catalytic Metal Structure with Acetic Acid 20 mg of Cu-TOP microsheets prepared according to EXAMPLE II and 4 mL of acetic acid (AA, 50%) were loaded into a 25 mL flask. The reaction solution was stirred at room temperature under Ar flow for 2 hours. The products were separated by centrifuging at 2000 rpm for 2 minutes. The supernatant was discarded. A total of 5 mL of ethanol (or another hydrophilic solvent such as acetone or methanol) was then added to the sediment, and the mixture was centrifuged at 2000 rpm for 3 minutes. The washing procedure was repeated twice to remove unreacted precursors and surfactant. The Cu-AA microsheets were stored in hydrophilic solvents (for example, acetone, ethanol, or methanol) before characterization.

It was found that the amounts of Cu-TOP microsheets may vary from 20 mg to 100 mg, and the volume of acetic acid used corresponds to the required reaction time.

Example III(c): Preparation of Catalytic Metal Structure with 1-Octanethiol 20 mg of Cu-TOP microsheets prepared according to EXAMPLE II and 4 mL of 1-octanethiol (SH, 49%) were loaded into a 25 mL flask. The reaction solution was stirred at room temperature under Ar flow for 2 hours. The products were separated by centrifuging at 2000 rpm for 2 minutes. The supernatant was discarded. A total of 5 mL of ethanol (or another hydrophilic solvent such as acetone or methanol) was added to the sediment, and the mixture was centrifuged at 2000 rpm for 3 minutes. The washing procedure was repeated twice to remove unreacted precursors and surfactant. The Cu-SH microsheets were stored in hydrophobic solvents (for example, hexane, toluene, or chloroform) before characterization.

It was found that the amounts of Cu-TOP microsheets may vary from 20 mg to 100 mg, and the volume of 1-octanethiol used corresponds to the required reaction time.

Example IV: Characterization and Electrochemical Measurements

The surface morphologies discussed herein were investigated by a scanning electron microscope (QUANTA FEG 650) from FEI with a field emitter as the electron source. A Bruker D8 Advance X-ray diffractometer with Cu Kα radiation operated at a tube voltage of 40 kV and a current of 40 mA was used to obtain X-ray diffraction (XRD) patterns. Gas chromatograph (GC 17A, SHIMADZU) was employed to analyze the concentration of gas products. The Fourier transform infrared (FTIR) spectra were obtained using FTIR spectrometer (NEXUS 670 FT-IR). Sample suspensions were drop casted on KBr crystal plates and allowed to dry as a film prior to the measurement. The separated gas products were analyzed by a thermal conductivity detector (for $H_2$) and a flame ionization detector (for CO). Liquid products were analyzed by high pure liquid chromatograph (HPLC, Dionex UltiMate 3000 (UHPLC+, Thermo Scientific).

Electrochemical measurements discussed herein were conducted using a potentiostat (VersaSTAT MC) in a two compartment electrochemical cell separated by an anion-exchange membrane (Selemion AMV). A platinum plate counter electrode and a leak-free Ag/AgCl reference electrode (innovative Instruments, diameter: 2.0 mm) were used in a three electrode configuration. Working electrodes were prepared by drop-casting 400 μg of each sample (Cu-TOP was dispersed in hexanes, while other Cu microsheets were dispersed in acetone) onto a carbon glassy electrode (Alfa Aesar: diameter of 1.0 $cm^2$) and drying under argon at room temperature. The working electrode and the counter electrode compartment hold 2.0 mL of electrolyte each, and the working compartment is sealed in order to allow measurements of gas products. All potentials herein were converted to the RHE scale by E(vs RHE)=E(vs Ag/AgCl)+0.205 V+0.0591×pH. The 0.1 M $KHCO_3$ electrolyte was prepared from $K_2CO_3$ saturated with $CO_2$ (pH 7.5).

During electrochemistry, $CO_2$ flowed through the working compartment at a rate of 5 sccm. During chronoamperometry, effluent gas from the cell went through the sampling loop of a GC to analyze the concentration of gas products. Quantification of the products was performed with the conversion factor derived from the standard calibration gases. Liquid products were analyzed afterward by HPLC. The concentrations are calculated through the software and are based on calibration curves which were developed for each individual component. Faradaic efficiencies were calculated from the amount of charge passed to produce each product divided by the total charge passed at a specific time or during the overall run.

Figure 2:
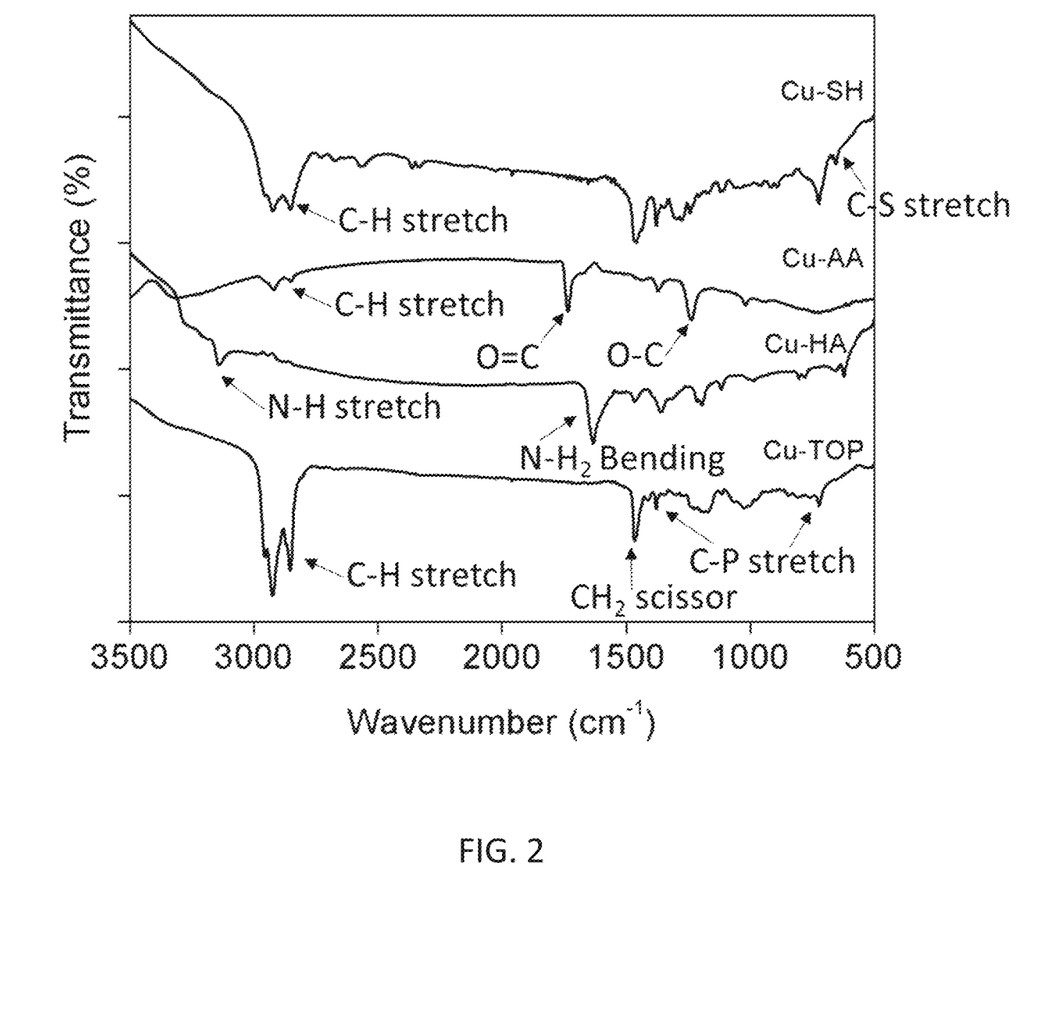
FIG. 2 shows FT-IR spectra corresponding to Cu microsheets prepared according to EXAMPLES II and III.

FT-IR spectra were used to characterize the surface chemistry of as-synthesized Cu microsheets with different ligands prepared according to EXAMPLES II and III, as shown in FIG. 2. The FT-IR spectra corresponding to the samples have obvious differences due to the microsheets' different surfaces. In the FT-IR spectrum of the Cu microsheets with trioctylphosphine (TOP), the bands at 2939 and 2877 cm-1 are due to —$CH_2$ stretching mode of TOP, and those around 1440 cm-1 correspond to —$CH_2$ scissor mode of TOP. The deformation band and stretching mode of C—P are located at 1440 cm-1 and 754 cm-1. After surface ligand exchange, the FT-IR spectrum shows the characteristic peaks as follows: the N—H stretching mode and N—H bending mode are found at around 3300 cm-1 and 1630 cm-1, which indicates that hydrazine completely replaced surface TOP on the Cu microsheets; while C=O and C—O stretching mode at 1680 cm-1 and 1230 cm-1 and C—S stretching mode at 710 cm-1 are attributed to acetic acid or 1-octanethiol, respectively. The above analysis indicates that surface ligand exchange successfully occurred for all reactions studied.

Figure 3:
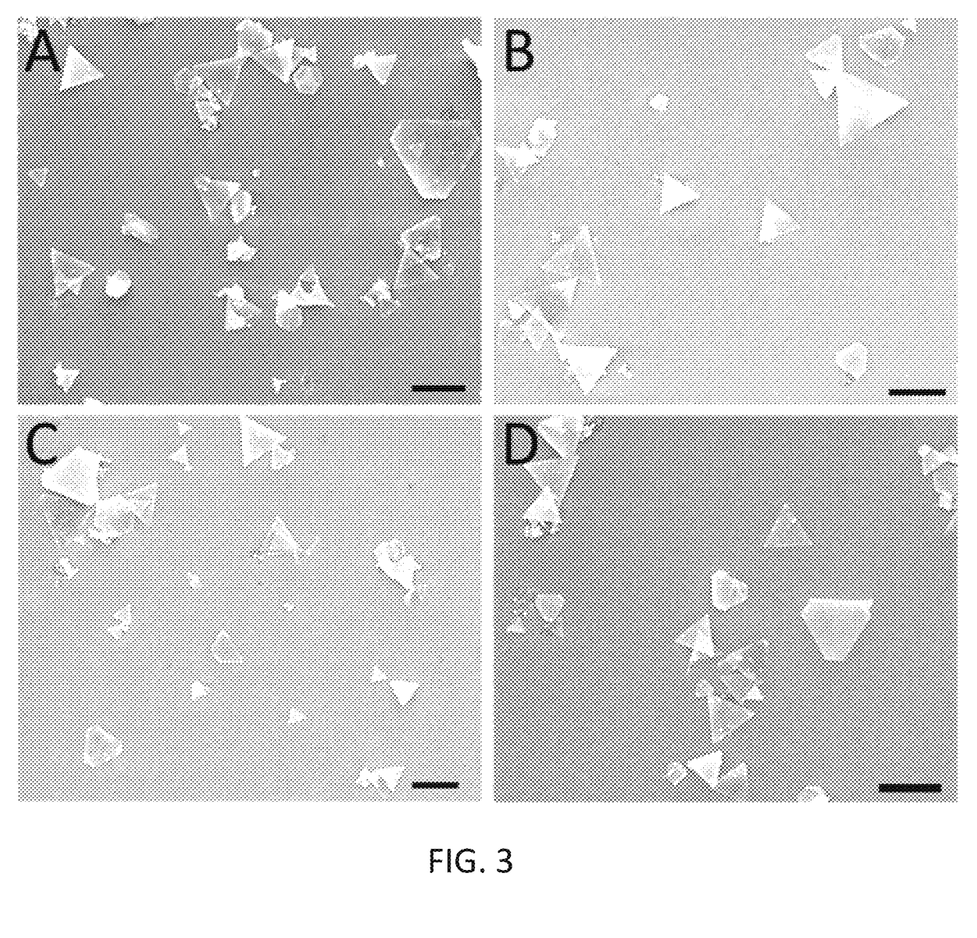
FIG. 3 shows the morphology and size characterization of Cu microsheets prepared according to EXAMPLES II and III.

FIG. 3 shows the morphology and size characterization of Cu microsheets with different ligands prepared according to EXAMPLES II and III. As shown in FIG. 3, no obvious morphology and size change has been found after shorter ligands (i.e., hydrazine shown in (B), acetic acid shown in (C), and 1-octanethiol shown in (D)) replaced TOP shown in (A). SEM results indicate that the majority of products are triangular sheets, and less than 10% of the sheets are polygon. The size range of sheets was between a few hundred nanometers and 13 micrometers.

Figure 4:
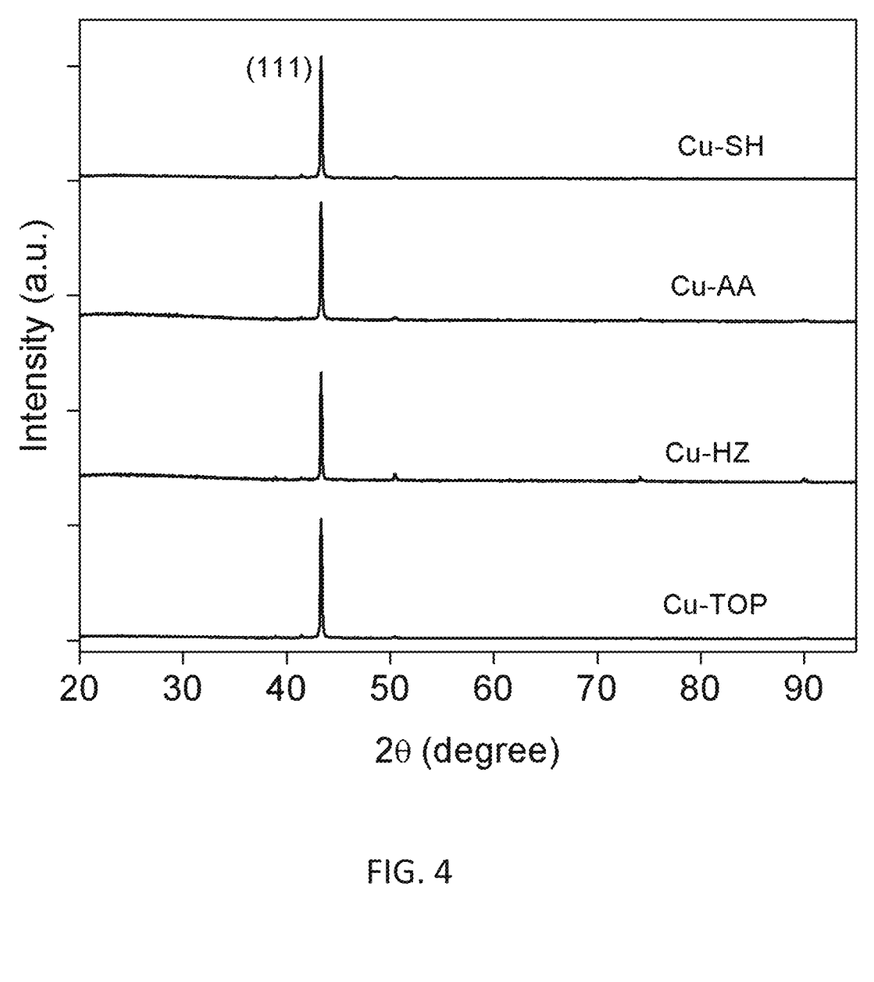
FIG. 4 shows the stability of Cu microsheets prepared according to EXAMPLES II and III.

An X-ray diffraction technique was employed to study the stability of Cu microsheets after surface ligand exchange, as shown in FIG. 4. The XRD sample was prepared by drying the Cu microsheet solution for each sample on a glass slide at room temperature. As a result, almost all of the Cu microsheets had a preferred orientation with {111} facets parallel to the glass substrate. Compared to the XRD pattern of fresh Cu microsheets, no obvious phase change was found after surface ligand exchange. Although weaker peaks of copper oxide were found, the amount of surface oxidation of Cu nanosheets seemed negligible.

As shown in FIG. 4, Cu microsheets had a single strong {111} diffraction peak, which is very different from that of standard fcc bulk Cu (PDF 04-003-7054). Generally, standard fcc bulk Cu XRD pattern has typically three crystalline facets: {111}, {200}, and {220}; while Cu microsheets has predominantly a single diffraction peak corresponding to {111} facet, which further confirms Cu microsheets possess high ratio of {111} facet. PDF 04-003-7054 is an X-ray diffraction index of standard bulk Cu.

Figure 5:
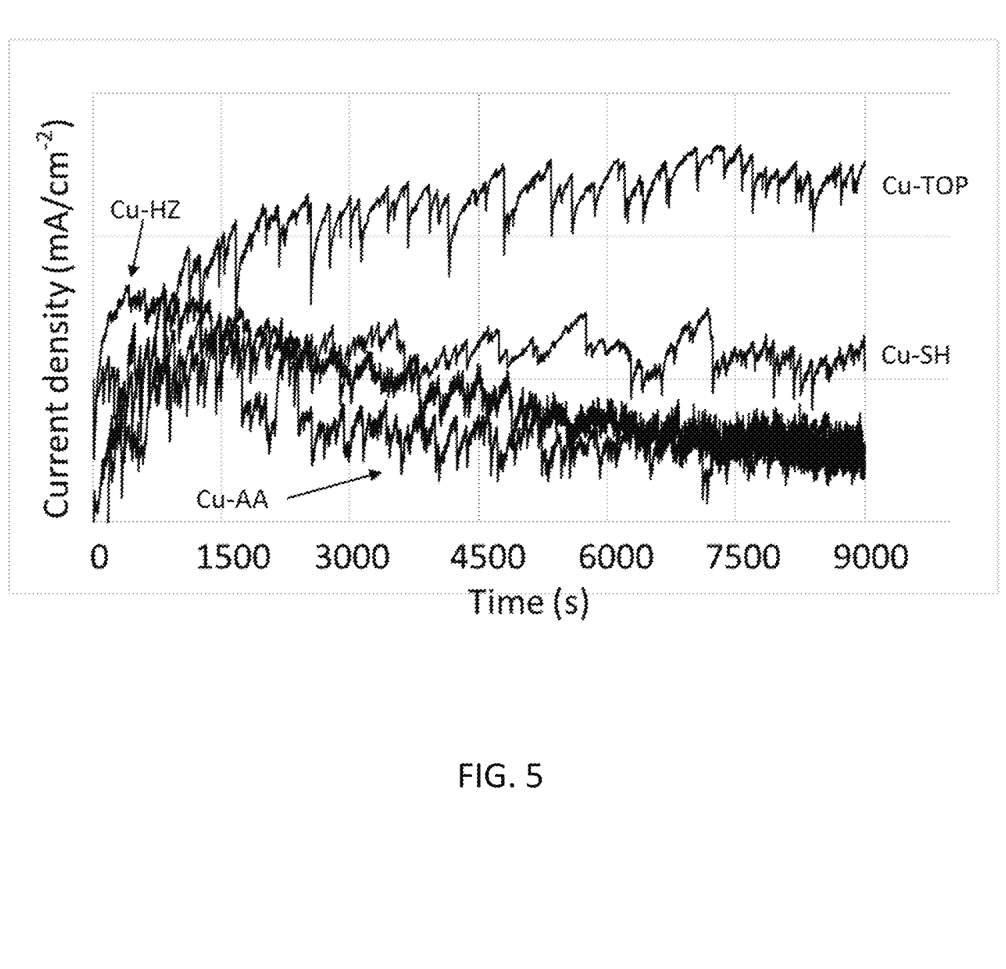
FIG. 5 shows the current vs. time profile of the electrolysis experiments performed according to EXAMPLE IV.

FIG. 5 shows the current vs. time profile of a representative electrolysis experiment at −1.25 V vs. RHE. As shown in FIG. 5, the current densities of all Cu microsheets studied remained relatively stable across the 2.5 hour-long testing. Because long chain ligands will restrict close contact with microsheets, the Cu-TOP microsheet had weaker conductivity and its average current density was −1.40 mA/$cm^2$. FIG. 5 also shows that shorter ligand modified-Cu microsheets showed enhanced current density. Their average current densities were −2.92 mA/$cm^2$ for Cu-HZ, −2.33 mA/$cm^2$ for Cu-SH, and −2.85 mA/$cm^2$ for Cu-AA. Compared by their average current densities, Cu-AA and Cu-HZ increased to twice and Cu-SH increased to 1.66 times that of Cu-TOP. Without wishing to be bound to any particular theory, it appears TOP molecules on the Cu structure surface have adverse effects on electrical conductivity, and therefore, the conductivity can be improved by replacing TOP molecules with shorter ligands.

Figure 6:
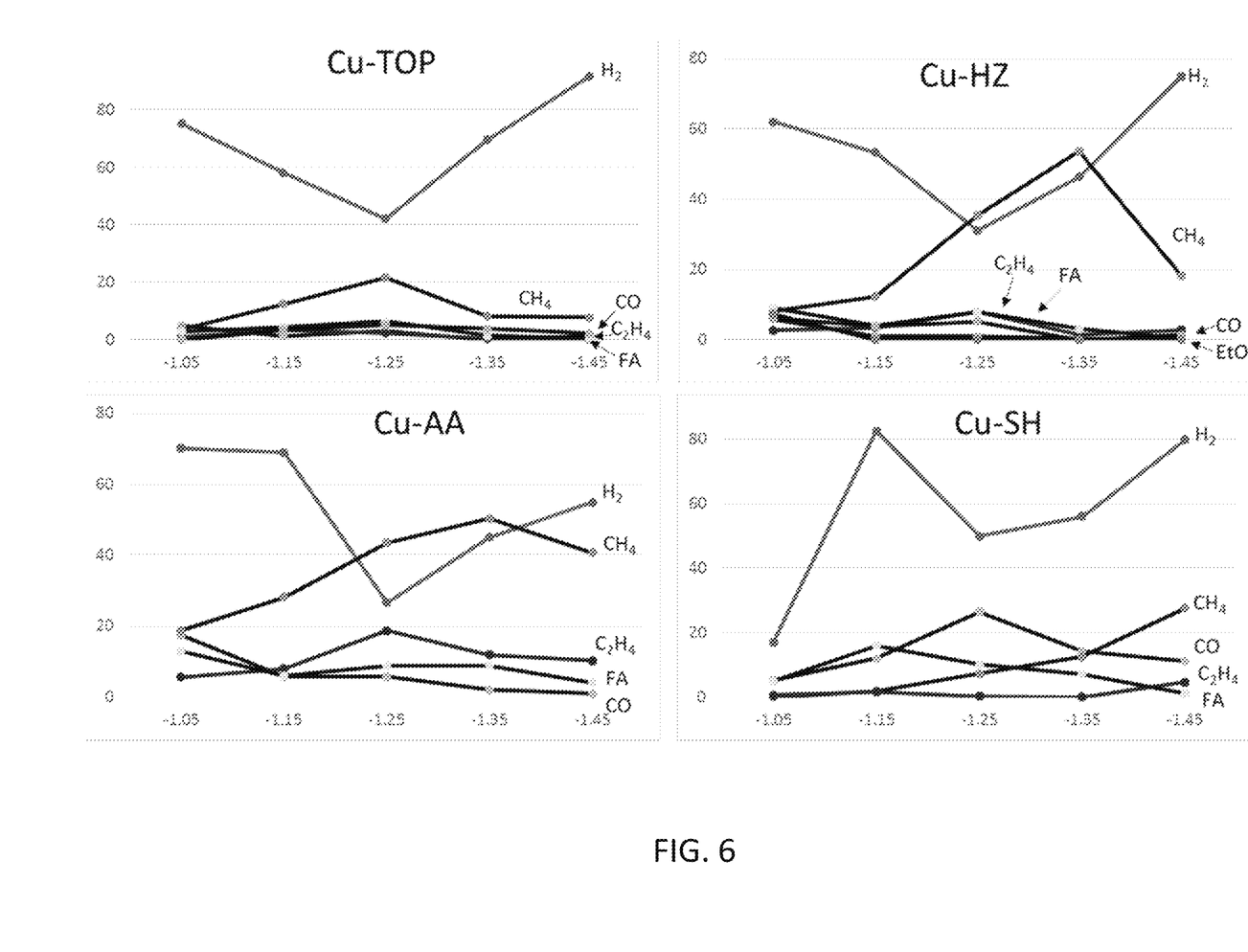
FIG. 6 shows the results of the electrochemical studies performed according to EXAMPLE IV.

To evaluate the catalytic performance of the Cu microsheets prepared according to EXAMPLES II and III as $CO_2$ reduction catalysts, the four different Cu microsheets were loaded onto glassy carbon to serve as working electrodes. FIG. 6 summarizes the results of the electrochemical studies for these four types of Cu electrodes, specifically (A) Cu-TOP, (B) Cu-HZ, (C) Cu-AA, and (D) Cu-SH, at different potentials vs. RHE. Apart from the competitive production of $H_2$, FIG. 6 at (A) indicates that the faradic efficiency (FE) of $CH_4$ reached 21% at −1.25 V when Cu-TOP was employed as a catalyst. FIG. 6 at (B) eveals that the Cu-HZ catalyst showed excellent selectivity for $CH_4$, which reached the maximum FE of 53.5% at −1.35 V. FIG. 6 at (C) shows that the Cu-AA catalyst was selective to $CH_4$ and $C_2H_4$, which reached the maximum FE of 50.3% at −1.35 V and 18.6% at −1.25 V, respectively. The FE of $CH_4$ increased to 2.6 and 2.4 times that of Cu-TOP catalysts for Cu-HZ and Cu-AA catalysts, respectively, which may indicate that hydrazine and acetic acid alert the surface energy of Cu surfaces and facilitate $CO_2$ reduction to $CH_4$. The Cu-SH catalyst was selective to CO gas products (FE=26%) at −1.25 V, as shown in FIG. 6 at (D). However, $H_2$ was the dominant gas product at different potentials. It is possible that the thiol group showed a stronger coordination ability with Cu atoms, which may have weakened CO for further reduction.

Based on the above, it was concluded that surface ligands play an important role in tuning the selectivity of catalytic metal structures for final products. In addition, it was concluded that the catalytic metal structures according to the present disclosure not only increase the conversion efficiency of $CO_2$ reduction reactions, but also improve product selectivity.

The invention claimed is:

1. A method for preparing a catalytic metal structure comprising:
   providing a preliminary metal structure comprising at least one preliminary surface ligand, and
   replacing the preliminary surface ligand with at least one surface ligand to provide the catalytic metal structure;
   wherein the at least one preliminary surface ligand comprises oleylamine.

2. The method according to claim 1, wherein the catalytic metal structure comprises a metal selected from the group consisting of copper, iron, cobalt, alloys thereof, and combinations thereof.

3. The method according to claim 1, wherein the catalytic metal structure comprises a metal nanoparticle.

4. The method according to claim 1, wherein providing the preliminary metal structure comprises preparing a metal complex, and
   reacting the metal complex with the preliminary surface ligand to provide the preliminary metal structure.

5. The method according to claim 1, wherein the at least one surface ligand is selected from the group consisting of hydrazine, ethylene diamine, propylene diamine, butane diamine, trimethylamine, acetic acid, propionic acid, butyric acid, valeric acid, octanethiol, ethanethiol, propanethiol, butanethiol, pentanethiol, hexanethiol, and combinations thereof.

6. The method according to claim 1, wherein the preliminary surface ligand has a first coordination strength, and the at least one surface ligand has a second coordination strength that is greater than the first coordination strength.

7. The method according to claim 1, wherein the preliminary surface ligand has a first length, and the at least one surface ligand has a second length that is shorter than the first length.

8. The method according to claim 1, wherein replacing the preliminary surface ligand of the preliminary metal structure with the one or more surface ligands comprises combining the preliminary metal structure with the one or more surface ligands.

9. The method according to claim 1, wherein the catalytic metal structure is configured to catalyze a $CO_2$ reduction reaction.

10. The method according to claim 9, wherein the catalytic metal structure has a product selectivity sufficient to provide such that a faradaic efficiency of at least one reaction product of the $CO_2$ reduction reaction at a potential vs. RHE of at least about 20%, wherein the at least one reaction product consists of $CH_4$.

11. The method according to claim 9, wherein the catalytic metal structure has a product selectivity sufficient to provide a faradaic efficiency of at least one reaction product of the $CO_2$ reduction reaction at a potential vs. RHE of at least about 40%, wherein the at least one reaction product consists of $CH_4$.

12. The method according to claim 9, wherein the catalytic metal structure has a product selectivity sufficient to provide such that a faradaic efficiency of at least one reaction product of the $CO_2$ reduction reaction at a potential vs. RHE of at least about 20%, wherein the at least one reaction product consists of CO.

13. A method for preparing a catalytic metal structure comprising:
    providing a preliminary metal structure comprising at least one preliminary surface ligand, and
    replacing the preliminary surface ligand with at least one surface ligand to provide the catalytic metal structure;
    wherein the at least one preliminary surface ligand comprises trioctylphosphine.

14. The method according to claim 13, wherein the catalytic metal structure comprises a metal selected from the group consisting of copper, iron, cobalt, alloys thereof, and combinations thereof.

15. The method according to claim 13, wherein the catalytic metal structure comprises a metal nanoparticle.

16. The method according to claim 13, wherein providing the preliminary metal structure comprises preparing a metal complex, and
    reacting the metal complex with the preliminary surface ligand to provide the preliminary metal structure.

17. The method according to claim 13, wherein the at least one surface ligand is selected from the group consisting of hydrazine, ethylene diamine, propylene diamine, butane diamine, trimethylamine, acetic acid, propionic acid, butyric acid, valeric acid, octanethiol, ethanethiol, propanethiol, butanethiol, pentanethiol, hexanethiol, and combinations thereof.

18. The method according to claim 13, wherein the preliminary surface ligand has a first coordination strength, and the at least one surface ligand has a second coordination strength that is greater than the first coordination strength.

19. The method according to claim 13, wherein the preliminary surface ligand has a first length, and the at least one surface ligand has a second length that is shorter than the first length.

20. The method according to claim 13, wherein replacing the preliminary surface ligand of the preliminary metal structure with the one or more surface ligands comprises combining the preliminary metal structure with the one or more surface ligands.

21. The method according to claim 13, wherein the catalytic metal structure is configured to catalyze a $CO_2$ reduction reaction.

22. The method according to claim 13, wherein the at least one preliminary surface ligand further comprises oleylamine.

* * * * *